United States Patent [19]
Ensminger et al.

[11] Patent Number: 5,506,195
[45] Date of Patent: Apr. 9, 1996

[54] SELECTIVE 1,3-CYCLOHEXANEDIONE CORN HERBICIDE

[75] Inventors: Michael P. Ensminger; John M. Shribbs, both of Petaluma, Calif.

[73] Assignee: Zeneca Limited, London, United Kingdom

[21] Appl. No.: 333,442

[22] Filed: Nov. 1, 1994

[51] Int. Cl.$^6$ .............................. A01N 35/06; A01N 41/12
[52] U.S. Cl. .................................................. 504/350
[58] Field of Search ................................. 504/350

[56] References Cited

U.S. PATENT DOCUMENTS

| | | | |
|---|---|---|---|
| 4,937,386 | 6/1990 | Ueda et al. | 568/31 |
| 5,006,158 | 4/1991 | Carter et al. | 71/98 |
| 5,318,947 | 6/1994 | Ort et al. | 504/310 |

*Primary Examiner*—S. Mark Clardy
*Attorney, Agent, or Firm*—Marian T. Thomson

[57] ABSTRACT

A method of selectively controlling undesirable vegetation in corn by applying an herbicidally effective amount of 2-(2'-nitro-4'-methylsulfonylbenzoyl)-1,3-cyclohexanedione to the locus of such vegetation.

5 Claims, No Drawings

1

SELECTIVE 1,3-CYCLOHEXANEDIONE CORN HERBICIDE

FIELD OF THE INVENTION

The present invention is directed to the use of 2-(2'-nitro-4'-methylsulfonylbenzoyl)-1,3-cyclohexanedione as a selective preemergence and postemergence herbicide in corn.

BACKGROUND OF THE INVENTION

The protection of crops from weeds and other vegetation which inhibit crop growth is a constantly recurring problem in agriculture. To help combat this problem researchers in the field of synthetic chemistry have produced an extensive variety of chemicals and chemical formulations effective in the control of such unwanted growth. Chemical herbicides of many types have been disclosed in the literature and a large number are in commercial use.

Unfortunately, many of such herbicides will exhibit phytotoxicity to the desired crop as well as to the weeds sought to be controlled. Thus, there is a long-standing need for selective herbicides which will control frequently occurring weeds but which will not adversely affect the crop plants when applied at herbicidally effective levels.

U.S. Pat. No. 5,006,158 to Carter et al. discloses 2'-nitro-substituted benzoyl cyclohexanediones having the structure:

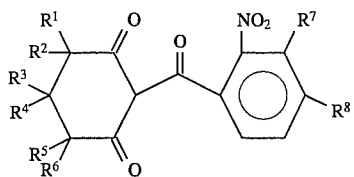

wherein $R^1$ and $R^3$–$R^6$ are hydrogen or alkyl, $R^2$ is hydrogen, alkyl or alkoxycarbonyl; $R^7$ is hydrogen or alkoxy; and $R^8$ is hydrogen, halogen, alkoxy, alkyl, $OCF_3$, cyano, nitro, haloalkyl, optionally substituted amino, optionally substituted aminosulfonyl, alkylcarbonyl, alkoxycarbonyl or $R^9(SO)_n$ wherein n is 0,1 or 2 and $R^9$ is substituted alkyl, phenyl or benzyl. Specifically disclosed, as Compound 26D, is 2-(2'-nitro- 4'-methylsulfonylbenzoyl)-1,3-cyclohexanedione. Such compound is demonstrated to be an effective preemergence and postemergence herbicide against a wide variety of grasses, broadleaf weeds and sedges when applied at a rate of 4.48 kg/ha.

It has now been discovered that such compound will effectively control a broad range of weeds typically associated with corn without exhibiting any substantial phytotoxic effect on the corn itself.

DESCRIPTION OF THE INVENTION

This invention is directed to a method of selectively controlling undesirable vegetation in corn, comprising application of an herbicidally effective amount of 2-(2'-nitro-4'-methylsulfonylbenzoyl)-1,3-cyclohexanedione (hereinafter NMSC) to the locus of such vegetation. As is employed herein, the term "herbicide" is used to denote a compound which controls or modifies the growth of plants. The term "herbicidally effective amount" is used to indicate the quantity of such compound which is capable of producing a controlling or modifying effect. Controlling or modifying effects include all deviations from natural development, for example: killing, retardation, leaf burn, albinism, dwarfing, and the like. The term "plants" refers to all physical parts of a plant, including seeds, seedlings, saplings, roots, tubers, stems, stalks, foliage, and fruits.

NMSC is a known compound and may be produced by methods such as those described in U.S. Pat. No. 5,006,158 to Carter et al.

In the practice of the present invention, NMSC is applied to the locus of the vegetation to be controlled. Application rates will depend on the particular plant species and degree of control desired. In general, application rates of between about 1 and about 1,000 g/ha may be employed, with rates of between about 20 and about 500 g/ha being preferred.

NMSC can be formulated in the same manner in which herbicides are generally formulated. The object of the formulation is to apply the compositions to the locus where control is desired by a convenient method. The "locus" is intended to include soil, as well as established vegetation.

In practice, NMSC is applied as a formulation containing various adjuvants and carriers known to or used in the industry for facilitating dispersion. The choice of formulation and mode of application for NMSC may affect its activity, and selection will be made accordingly. The NMSC may thus be formulated as wettable powders, as flowable formulations, as emulsions, as granular formulations, as water dispersible granules, as powders or dusts, or as controlled release forms such as microcapsules. These formulations may contain as little as about 0.5% to as much as about 95% or more by weight of NMSC. The optimum amount in any particular formulation will depend upon the materials in the formulation and the type of seeds or plants to be controlled.

Wettable powders (WP) are in the form of finely divided particles which disperse readily in water or other liquid carriers. The particles contain the active ingredient retained in a solid matrix. Typical solid matrices include fuller's earth, kaolin clays, silicas, and other readily wet organic or inorganic solids. Wettable powders normally contain about 5% to about 95% of the active ingredient plus a small amount of wetting, dispersing, or emulsifying agent.

Flowable formulations, also known as Suspension Concentrates (SC), are stable suspensions of active ingredient(s) intended for dissolution before use. This type of formulation consists of a dispersion of finely divided active ingredient(s) which may be practically insoluble or only slightly soluble in water or in organic solvents chosen as the diluent. It also contains inert materials such as dispersants, wetting agents, suspending aids and diluent. In general, flowable formulations tend to be creamy in appearance and readily mixable with water.

Emulsions, also known as emulsifiable concentrates (EC), are heterogeneous dispersions of one liquid in another liquid with which it is incompletely miscible. There are two common types, a dispersion of fine globules of an organic liquid in water (O/W type), and, less commonly, a dispersion of globules of an aqueous liquid in oil (W/O type). A stable mixture is produced by the addition of appropriate emulsifying agents. Typically, this type of formulation will contain 1 to 90% active ingredient.

Granular formulations, generally referred to as Impregnated Granular Formulations (GR) contain active ingredients impregnated in carriers. Inert materials of granular formulations include extrudates, relatively coarse particles ("carriers"), and surface active agents. Typical carriers of granular formulations include: sand, fuller's earth, vermiculite, perlite, and other organic or inorganic materials which can be coated with the active compound. Typical surface active agents are: 1) heavy aromatic naphthas, kerosene and other petroleum fractions, 2) vegetable oils, and 3) stickers, such as dextrins, glue, or synthetic resins. Granular formulations are usually applied to weeds without being diluted.

Water Dispersible Granules (WG or WDG) formulations consist of small granules to be disintegrated and dispersed in water prior to application. Granules can be formed either by agglomeration or through the use of elevated pressure, for example, extrusion. Surface active agents, such as dispersants and wetting agents, are essential ingredients of the formulation. Clays, silicas and starch, among others, can be used as carriers.

Powders or dusts are free-flowing admixtures of the active ingredient with finely divided solids such as talc, clays, flours, and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust, and granular carbon. Shell or membrane materials include natural and synthetic rubbers, cellulosic materials, styrene-butadiene copolymers, polyacrylonitriles, polyacrylates, polyesters, polyamides, polyureas, polyurethanes, and starch xanthates.

Other useful formulations for herbicidal applications include simple solutions, sometimes described as flowable formulations, of the active ingredient in a solvent in which it is completely soluble at the desired concentration, such as water, acetone, alkylated naphthalenes, xylene, and other organic solvents. Pressurized sprayers, wherein the active ingredient is dispersed in finely-divided form as a result of vaporization of a low boiling dispersant solvent carrier, may also be used.

Many of these formulations include wetting, dispersing or emulsifying agents. Examples of these agents are alkyl and alkylaryl sulfonates and sulfates and their salts, polyhydric alcohols, polyethoxylated alcohols, esters, and fatty amines. These agents, when used, normally comprise from 0.1% to 15% by weight of the formulation.

Each of the above formulations can be prepared as a package containing the herbicide together with other ingredients of the formulation (diluents, emulsifiers, surfactants etc.). The formulations can also be prepared by a tank mix method in which the ingredients are obtained separately and combined at the grower site.

These formulations can be applied by conventional methods to the areas where control is desired. Dust and liquid compositions, for example, can be applied by the use of power dusters, boom and hand sprayers, and spray dusters. The formulations can also be applied from airplanes as a dust or a spray or by rope wick applications. To modify or control growth of germinating seeds or emerging seedlings, dust and liquid formulations can be distributed in the soil to a depth of at least one centimeter below the soil surface or can be applied to the soil surface only, by spraying or sprinkling. The formulations can also be applied by addition to irrigation water, permitting penetration of the formulations into the soil together with the irrigation water. Dust compositions, granular compositions, or liquid formulations applied to the surface of the soil can be distributed below the surface of the soil by conventional means such as discing, dragging or mixing operations.

EXAMPLES

The following Examples are intended to further illustrate the present invention and are not intended to limit the scope of this invention in any manner whatsoever.

Example 1

NMSC was applied (at the rates listed in Table I below) preemergence to aluminum flats (measuring 16×23×7 cm deep) containing loam soil in which the following species had been sown: *Setaria faberi* (giant foxtail) ("SETFA"); *Sorghum bicolor* (shattercane) ("SORVU"); *Abutilon theophrasti* (velvetleaf) ("ABUTH"); *Amaranthus retroflexus* (redroot pigweed) ("AMARE"); *Chenopodium album* (lambsquarters) ("CHEAL"); *Helianthus annuus* (sunflower) ("HELAN"); *Polygonum pensylvanicum* (Pennsylvania smartweed) ("POLPY"); *Ipomoea purpurea* (tall morningglory) ("PHBPU"); *Xanthium pensylvanicum* (cocklebur) ("XANPE"); *Cyperus esculentus* (yellow nutsedge) ("CYPES"); and corn, *Zea mays* 'Dekalb 656' ("ZEAMX DK656") and 'Garst 8711' ("ZEAMX GA8711"). The soil was fortified with fertilizer (17-17-17) and treated with a fungicide, Captan 80W, prior to seeding. All of the herbicides were applied preemergence with the carrier volume of 234 L/ha (25 gal/A).

After application of NMSC, the flats were placed in a greenhouse. Injury to corn was rated at 8 and 27 days after treatment ("DAT"). Injury was evaluated as percent control, with percent control being the total injury to the plants due to all factors including: inhibited emergence, stunting, malformation, albinism, chlorosis, and other types of plant injury. The control ratings range from 0 to 100 percent, where 0% represents no effect with growth equal to the untreated control and where 100% represents complete kill.

The results observed (as a mean of 3 replications) are summarized in Table I below.

TABLE I

| RATE (G/HA) | 8 DAT | | 27 DAT | | | | | |
|---|---|---|---|---|---|---|---|---|
| | ZEAMX DK656 | ZEAMX GA8711 | SETFA | SORVU | ABUTH | AMARE | CHEAL | HELAN |
| 31 | 0 | 0 | 0 | 0 | 100 | 98 | 70 | 100 |
| 63 | 0 | 0 | 10 | 5 | 100 | 99 | 85 | 100 |
| 125 | 0 | 0 | 0 | 50 | 100 | 100 | 100 | 100 |
| 250 | 0 | 0 | 25 | 95 | 100 | 100 | 100 | 100 |

TABLE I-continued

| 500 | 10 | 0 | 65 | 100 | 100 | 100 | 100 | 100 |

| | | | | 27 DAT | | | | |
| --- | --- | --- | --- | --- | --- | --- | --- | --- |
| | RATE (G/HA) | POLPY | PHBPU | XANPE | CYPES | ZEAMX DK656 | ZEAMX GA877 | |
| | 31 | 90 | 63 | 55 | 90 | 0 | 0 | |
| | 63 | 100 | 75 | 100 | 95 | 0 | 0 | |
| | 125 | 100 | 99 | 100 | 97 | 0 | 0 | |
| | 250 | 100 | 100 | 100 | 98 | 0 | 0 | |
| | 500 | 100 | 100 | 100 | 99 | 0 | 0 | |

Example 2

Employing a procedure essentially identical to that described in Example 1 except that a silty clay loam soil was employed, NMSC was applied (at the rates listed in Table II below) preemergence to aluminum flats containing the following species: ABUTH; PHBPU; AMARE; POLPY; CYPES; SETFA; *Echinochloa crus-galli* (watergrass) ("ECHCG"); SORVU; and corn hybrids ZEAMX DK656, ZEAMX GA8711, and Pioneer 3475 ("ZEAMX PI3475"). After application, the flats were placed in a greenhouse and the results evaluated after 31 days.

The results observed (as a mean of 3 replications) are summarized in Table II below.

TABLE II

| RATE (G/HA) | ABUTH | PHBPU | AMARE | POLPY | CYPES | SETFA | ECHCG | SORVU | ZEAMX DK656 | ZEAMX GA8711 | ZEAMX PI3475 |
| --- | --- | --- | --- | --- | --- | --- | --- | --- | --- | --- | --- |
| 31 | 98 | 0 | 20 | 80 | 65 | 0 | 33 | 0 | 0 | 0 | 0 |
| 63 | 100 | 0 | 20 | 73 | 92 | 7 | 7 | 7 | 0 | 0 | 0 |
| 125 | 80 | 17 | 68 | 83 | 65 | 33 | 0 | 18 | 0 | 0 | 0 |
| 250 | 100 | 22 | 100 | 98 | 98 | 0 | 100 | 35 | 0 | 0 | 0 |
| 500 | 100 | 65 | 100 | 98 | 98 | 15 | 100 | 65 | 5 | 0 | 0 |

Example 3

NMSC was applied (at the rates listed in Table III below) preemergence to aluminum flats (measuring 20×10×6 cm deep) containing soil comprising 2 parts of clay loam to 1 part sandy loam. Prior to application, the following species had been sown: *Ipomea spp.* (morning glory) ("IPOSS"); XANPE; ABUTH; AMARE; *Polygonum lapathifolum* (smartweed) ("POLLA"); *Sesbania exaltata* (sesbania) ("SEBEX"); *Cassia obtusifolia* (sicklepod) ("CASOB"); SETFA; SORVU; ECHCG; CYPES; and corn hybrid 'DeKalb T-1100' ("ZEAMX DK1100"). The flats were placed in a greenhouse and evaluated 17 days after treatment.

The results observed (as a mean of 2 replications) are summarized in Table III below.

TABLE III

| RATE (G/HA) | IPOSS | XANPE | ABUTH | SEBEX | CASOB | POLLA | AMARE | SORVU |
| --- | --- | --- | --- | --- | --- | --- | --- | --- |
| 125 | 68 | 85 | 100 | 93 | 45 | 95 | 100 | 88 |
| 250 | 83 | 95 | 100 | 100 | 73 | 100 | 100 | 98 |
| 500 | 95 | 100 | 100 | 100 | 85 | 98 | 100 | 98 |
| 1000 | 100 | 100 | 100 | 100 | 95 | 98 | 100 | 100 |

| RATE (G/HA) | CYPES | SETFA | ECHCG | ZEAMX DK1100 |
| --- | --- | --- | --- | --- |
| 125 | 90 | 35 | 95 | 0 |
| 250 | 90 | 58 | 100 | 0 |
| 500 | 90 | 78 | 100 | 3 |
| 1000 | 93 | 90 | 100 | 35 |

Example 4

Twelve days after the seeds were sown in aluminum flats (containing soil comprising 2 parts sandy loam to 1 part peat), NMSC was applied (at the rates listed in Table IV)

postemergence to plant species listed in Example 3. The flats were placed in a greenhouse and evaluated 17 days after treatment.

The results observed (as a mean of 2 replications) are summarized in Table IV below.

TABLE IV

| RATE (G/HA) | IPOSS | XANPE | ABUTH | SEBEX | CASOB | POLLA | AMARE | SORVU |
|---|---|---|---|---|---|---|---|---|
| 63 | 100 | 93 | 100 | 100 | 68 | 93 | 100 | 88 |
| 125 | 100 | 98 | 100 | 100 | 85 | 100 | 100 | 92 |
| 250 | 100 | 93 | 100 | 100 | 93 | 95 | 100 | 95 |
| 500 | 100 | 100 | 100 | 100 | 98 | 100 | 100 | 100 |

| RATE (G/HA) | CYPES | SETFA | ECHCG | ZEAMX DK1100 |
|---|---|---|---|---|
| 63 | 85 | 55 | 92 | 0 |
| 125 | 90 | 78 | 95 | 2 |
| 250 | 93 | 95 | 100 | 5 |
| 500 | 97 | 98 | 100 | 40 |

Example 5

NMSC was applied (at the rates listed in Table V) preemergence to aluminum flats (measuring 20×10×6 cm deep) containing soil comprising 1 part clay loam to 1 part sandy loam. Prior to application, the following species had been sown: IPOSS; SORVU; CASOB; SETFA; AMARE; soybean, *Glycine max*, 'Corsoy' ("GLXMA CORSOY"); corn hybrid Stauffer 7751 ("ZEAMX ST7751").

The flats were placed in a greenhouse and evaluated 20 days after treatment. The results observed (as a mean of 2 replications) are summarized in Table V below.

TABLE V

| RATE (G/HA) | IPOSS | SORVU | CASOB | SETFA | AMARE | GLXMA CORSOY | ZEAMX ST7751 |
|---|---|---|---|---|---|---|---|
| 31 | 33 | 0 | 15 | 10 | 98 | 45 | 0 |
| 63 | 35 | 30 | 15 | 13 | 98 | 55 | 0 |
| 125 | 63 | 48 | 30 | 35 | 100 | 68 | 0 |
| 250 | 90 | 85 | 65 | 58 | 98 | 83 | 0 |
| 500 | 99 | 100 | 83 | 80 | 100 | 93 | 0 |

The above results indicate the unexpected corn selectivity of NMSC.

What is claimed is:

1. A method of selectively controlling undesirable vegetation in corn comprising applying an herbicidally effective amount of 2-(2'-nitro-4'-methylsulfonylbenzoyl)-1,3-cyclohexanedione to the locus of such vegetation.

2. A method in accordance with claim 1 wherein the 2-(2'-nitro-4'-methylsulfonylbenzoyl)-1,3-cyclohexanedione is applied at a rate of between about 1 and about 1000 grams per hectare.

3. A method in accordance with claim 2 wherein the 2-(2'-nitro-4'-methylsulfonylbenzoyl)-1,3-cyclohexanedione is applied at a rate of between about 20 and about 500 grams per hectare.

4. A method in accordance with claim 1 wherein the 2-(2'-nitro-4'-methylsulfonylbenzoyl)-1,3-cyclohexanedione is applied preemergence.

5. A method in accordance with claim 1 wherein the 2-(2'-nitro-4'-methylsulfonylbenzoyl)-1,3-cyclohexanedione is applied postemergence.

* * * * *